US012023618B2

United States Patent
Ueda et al.

(10) Patent No.: US 12,023,618 B2
(45) Date of Patent: Jul. 2, 2024

(54) FILTER REINFORCING MATERIAL AND FILTER MEDIUM FOR DEODORIZING FILTER COMPRISING SAME

(71) Applicants: KUREHA LTD., Ritto (JP); TOYOBO CO., LTD., Osaka (JP)

(72) Inventors: Taiki Ueda, Ritto (JP); Kotaro Shimokawa, Otsu (JP)

(73) Assignees: KUREHA LTD., Ritto (JP); TOYOBO CO., LTD., Osaka (JP)

( * ) Notice: Subject to any disclaimer, the term of this patent is extended or adjusted under 35 U.S.C. 154(b) by 923 days.

(21) Appl. No.: 16/978,858

(22) PCT Filed: Mar. 5, 2019

(86) PCT No.: PCT/JP2019/008503
§ 371 (c)(1),
(2) Date: Sep. 8, 2020

(87) PCT Pub. No.: WO2019/176628
PCT Pub. Date: Sep. 19, 2019

(65) Prior Publication Data
US 2021/0039028 A1 Feb. 11, 2021

(30) Foreign Application Priority Data
Mar. 12, 2018 (JP) ................. 2018-043778

(51) Int. Cl.
*B01D 39/14* (2006.01)
*A61L 9/014* (2006.01)
(Continued)

(52) U.S. Cl.
CPC .......... *B01D 46/0038* (2013.01); *A61L 9/014* (2013.01); *B01D 39/16* (2013.01); *B01D 39/2062* (2013.01); *B01D 46/0036* (2013.01); *B32B 5/022* (2013.01); *B32B 5/16* (2013.01); *B32B 5/26* (2013.01); *B32B 7/12* (2013.01); *D04H 1/559* (2013.01); *A61L 2209/14* (2013.01); *A61L 2209/22* (2013.01); *B01D 2239/0225* (2013.01); *B01D 2239/0233* (2013.01); *B01D 2239/0407* (2013.01); *B01D 2239/045* (2013.01); *B01D 2239/0618* (2013.01); *B01D 2239/0636* (2013.01); *B01D 2239/0668* (2013.01); *B01D 2275/10* (2013.01);
(Continued)

(58) Field of Classification Search
CPC ................ B01D 46/0038; B01D 39/16; B01D 39/2062; B01D 46/0036; B01D 2239/0225; B01D 2239/0233; B01D 2239/0407; B01D 2239/045; B01D 2239/0618; B01D 2239/0636; B01D 2239/0668; B01D 2275/10; B01D 2239/0442; B01D 2239/0457; B01D 2239/064; B01D 2239/086; B01D 39/1623; B01D 2239/0622; B01D 2239/0627; B01D 2239/1241; B01D 39/163; B01D 2239/0654; B01D 2239/1225; B01D 2239/1233; B01D 53/04; A61L 9/014; A61L 2209/14; A61L 2209/22; B32B 5/022; B32B 5/16; B32B 5/26; B32B 7/12; B32B 2262/0253; B32B 2264/108; B32B 2307/758; B32B 2250/20; B32B 2262/0238; B32B 2262/0269; B32B 2250/02; B32B 2262/0246; B32B 2262/0261; B32B 2262/0276; B32B 2262/0284; B32B 2262/0292; B32B 2262/04; B32B 2262/062; B32B 2307/732; B32B 2262/08; B32B 2262/12; B32B 2307/718; D04H 1/559; D10B 2321/022; D10B 2505/04
USPC ...................... 96/134, 135, 154; 55/524, 527
See application file for complete search history.

(56) References Cited

U.S. PATENT DOCUMENTS 5,486,410 A * 1/1996 Groeger ............... B01D 39/163
442/364
5,674,339 A * 10/1997 Groeger .................... B32B 5/08
156/283
(Continued)

FOREIGN PATENT DOCUMENTS

EP    1627618 A1 *  2/2006
JP   2008-231597 A   10/2008
(Continued)

OTHER PUBLICATIONS

International Search Report dated Jun. 4, 2019, issued in counterpart International Application No. PCT/JP2019/008503. (2 pages).
(Continued)

*Primary Examiner* — Frank M Lawrence, Jr.
(74) *Attorney, Agent, or Firm* — WHDA, LLP

(57) ABSTRACT

A filter reinforcing material is disclosed that does not cause peeling or pleat adhesion at the time of pleating, is excellent in pleating, and has high stiffness. A filter reinforcing material includes a bonding layer comprising a thermal bonded nonwoven including thermal bondable short fibers, and a reinforcing layer comprising a nonwoven including high-melting fibers having a higher melting point than a melting point of the thermal bondable short fibers having the lowest melting point in the bonding layer by 30° C. or more. Further, the bonding layer preferably comprises two or more kinds of thermal bondable short fibers with a fineness difference of more than or equal to 5 dtex.

8 Claims, No Drawings

(51) Int. Cl.
  *A61L 9/16* (2006.01)
  *B01D 39/16* (2006.01)
  *B01D 39/20* (2006.01)
  *B01D 46/00* (2022.01)
  *B32B 5/02* (2006.01)
  *B32B 5/16* (2006.01)
  *B32B 5/26* (2006.01)
  *B32B 7/12* (2006.01)
  *D04H 1/559* (2012.01)

(52) U.S. Cl.
  CPC . *B32B 2262/0253* (2013.01); *B32B 2264/108* (2013.01); *B32B 2307/758* (2013.01); *D10B 2321/022* (2013.01); *D10B 2505/04* (2013.01)

(56) References Cited

U.S. PATENT DOCUMENTS

| | | | | |
|---|---|---|---|---|
| 11,511,235 | B2* | 11/2022 | Jeong | B01D 39/16 |
| 2005/0016382 | A1 | 1/2005 | Miyahara et al. | |
| 2013/0037481 | A1 | 2/2013 | Lalouch et al. | |
| 2013/0193063 | A1 | 8/2013 | Ng et al. | |
| 2013/0199141 | A1* | 8/2013 | Hamada | D04H 1/559 |
| | | | | 55/486 |
| 2016/0175753 | A1* | 6/2016 | Hidaka | A61L 9/16 |
| | | | | 96/135 |
| 2016/0288034 | A1 | 10/2016 | Miyauchi et al. | |
| 2018/0028953 | A1* | 2/2018 | Tanaka | B01D 46/10 |
| 2020/0018001 | A1* | 1/2020 | Kojima | D04H 1/732 |

FOREIGN PATENT DOCUMENTS

| | | |
|---|---|---|
| JP | 2012-125714 A | 7/2012 |
| JP | 2015-44183 A | 3/2015 |
| JP | 2015-139720 A | 8/2015 |
| JP | 2016-137801 A | 8/2016 |
| WO | 2017208952 A1 | 12/2017 |

OTHER PUBLICATIONS

Office Action dated Jan. 28, 2022, issued in counterpart CN Application No. 201980018262.1, with English machine translation. (20 pages).

Extended (Supplementary) European Search Report dated Nov. 5, 2021, issued in counterpart EP Application No. 19766620.9. (9 pages).

Office Action dated Jul. 2, 2021, issued in counterpart CN Application 201980018262.1, with English Translation. (20 pages).

* cited by examiner

FILTER REINFORCING MATERIAL AND FILTER MEDIUM FOR DEODORIZING FILTER COMPRISING SAME

TECHNICAL FIELD

The present invention relates to a filter reinforcing material and a filter medium for deodorizing filter comprising same.

BACKGROUND ART

Conventionally, as a high-performance air filter medium, meltblown nonwoven made by assembling various fine fibers such as polypropylene fine fibers and the like has been used. Since the meltblown nonwoven is made of fine fibers, filtration performance is high, but strength or stiffness is low. Thus, in order to reinforce such the air filter medium having low strength or low stiffness, it has been widely worked to attach a reinforcing material having high strength and high stiffness to the air filter medium. For example, Patent Literature 1 discloses a filter medium for deodorizing filter comprising a filter medium consisting of laminated structure where 10 to 450 g/m$^2$ of adsorbent layer consisting of adsorbents and adhesives is sandwiched between base material layers, wherein at least one layer of the base material layers is a laminated sheet laminating a nonwoven made of thermal fusion bondable long fibers and having metsuke (mass per unit area) 5 to 40 g/m$^2$ and a meltblown nonwoven; the adsorbent layer and the nonwoven made of thermal fusion bondable long fibers in the laminated sheet are laminated adjacent to each other and thermally fusion-bonded.

CITATION LIST

Patent Literature

Patent Literature 1: JP2015-44183A

SUMMARY OF THE INVENTION

Problems to be Solved by the Invention

In recent years, the filter medium, which is used for various air filters for automobiles and households, is required to have higher functionality, diversification, smaller size, and higher processing capacity. In addition, the filter medium is generally subjected to pleating in order to increase the filtration area, thus improvement of the workability of pleating is also an urgent task. In particular, in order to maximize the characteristics of the adsorbents, for no peeling at the time of pleating even if the coating area of the adhesives which coats adsorbents is minimized, and for being able to maintaining the shape of the filter medium even if the processing wind speed is large, the filter medium with higher stiffness is required than ever.

On the other hand, in the pleating process of the filter medium, heating process is generally performed to fix the shape of the creased part. However, if the formed pleats adhere by heat treatment during heat setting, the pleating property becomes worse.

Therefore, the present invention aims to provide a filter reinforcing material that does not cause peeling or pleat adhesion at the time of pleating, is excellent in pleating, and has high stiffness.

Solution to the Problems

As a result of thorough research for solving the above-described problems, the present inventors have found that the above-described problems might be solved by a filter reinforcing material comprising, a bonding layer comprising a thermal bonded nonwoven including thermal bondable short fibers, and a reinforcing layer comprising a nonwoven including high-melting fibers having a higher melting point than a melting point of the thermal bondable short fibers having the lowest melting point in the bonding layer by 30° C. or more. Accordingly, the present inventors have completed the present invention.

Thus, the filter reinforcing material of the present invention has gist in the following points.

[1] A filter reinforcing material comprising,
    a bonding layer comprising a thermal bonded nonwoven including thermal bondable short fibers, and
    a reinforcing layer comprising a nonwoven including high-melting fibers having a higher melting point than a melting point of the thermal bondable short fibers having the lowest melting point in the bonding layer by 30° C. or more.

[2] The filter reinforcing material according to [1], wherein the bonding layer comprises two or more kinds of thermal bondable short fibers with a fineness difference of more than or equal to 5 dtex.

[3] The filter reinforcing material according to [1] or [2], wherein the reinforcing layer comprises the high-melting fibers by more than or equal to 60 weight % out of 100 weight % of fibers contained in the reinforcing layer.

[4] The filter reinforcing material according to any one of items [1] to [3], wherein, melting point of the thermal bondable short fibers is 80 to 150° C., and content of the thermal bondable short fibers with a melting point of 80 to 150° C. is 60 to 100 weight % out of 100 weight % of fibers contained in the bonding layer.

[5] The filter reinforcing material according to any one of items [1] to [4], wherein average fineness of fibers contained in the reinforcing layer is larger than average fineness of fivers fibers contained in the bonding layer.

[6] The filter reinforcing material according to any one of items [1] to [5], wherein the bonding layer and the reinforcing layer are integrated by thermal fusion bonding.

[7] The filter reinforcing material according to any one of items [1] to [6], wherein the thermal bondable short fibers are composite fibers with core-sheath structure, eccentric structure, or side-by-side structure.

Further, the filter medium for deodorizing filter of the present invention has gist in the following points.

[8] A filter medium for deodorizing filter comprising, the filter reinforcing material according to any one of items [1] to [7], an adsorbent layer comprising adsorbents laminated on the side of the bonding layer of the filter reinforcing material, and a base material laminated to sandwich the absorbent layer with the filter reinforcing material.

Advantageous Effects of the Invention

According to the present invention, there is provided the filter reinforcing material that does not cause peeling or pleat adhesion at the time of pleating, is excellent in pleating, and has high stiffness.

DESCRIPTION OF EMBODIMENTS

A filter reinforcing material of the present invention is characterized by comprising; a bonding layer comprising a thermal bonded nonwoven including thermal bondable short fibers, and a reinforcing layer comprising a nonwoven including high-melting fibers having a higher melting point than a melting point of the thermal bondable short fibers having the lowest melting point in the bonding layer by 30° C. or more.

In the present invention, the difference of a melting point between the thermal bondable short fibers used for the bonding layer and the high-melting fibers used for the reinforcing layer is important. By setting the difference of a melting point to higher than or equal to 30° C., it is possible to improve adhesive strength with an adsorbent layer on the side of the bonding layer, and it is possible to improve pleating property (for example, suppression of pleat adhesion at the time of heat setting) on the side of the reinforcing layer, respectively.

Further, since the thermal bondable short fibers for the bonding layer are short fibers in the filter reinforcing material of the present invention, entanglement between fibers becomes more complicated and the voids between fibers becomes narrower than in the case where the thermal bondable short fibers are long fibers. That prevents adsorbents from dropping out, improves peel strength, and suppresses peeling at the time of pleating. In addition, the complicated entanglement between fibers adds stiffness to the filter reinforcing material itself, improves bending strength, and contributes to prevention of deformation during use. Furthermore, pressure loss of a filter medium for deodorizing filter is reduced due to the improvement of stiffness of the filter reinforcing material itself and the effect of suppressing pleat adhesion.

Furthermore, the use of the thermal bonded nonwoven including the thermal bondable short fibers as the bonding layer has the following advantages over conventional adhesives (for example, powder, spray, sheet and the like).

(1) Contribute to improving stiffness; Conventional adhesives basically were spot-gluing, thus did not contribute to improving stiffness of the filter reinforcing material and the filter medium for deodorizing filter. However, in the present invention, the thermal bonded nonwoven is used, thus stiffness of the thermal bonded nonwoven itself is added. Thereby, that contributes to improving stiffness of the filter reinforcing material and the filter medium for deodorizing filter.

(2) Characteristic of adsorbents can be utilized more effectively; As discussed above, since the conventional adhesives were spot-gluing, filtration performance was not exhibited, and thus that did not contribute to dust collecting performance of the filter medium for deodorizing filter. However, since the thermal bonded nonwoven is used, filtration performance is also exhibited in the bonding layer. Thereby, the amount of sticking dust to adsorbents in the adsorbent layer can be reduced, and performance of adsorbents can be utilized more effectively.

(3) Effective in suppressing cracks when forming pleats; Since the conventional adhesives were spot-gluing, when the adhesives touched adsorbents, it tended to clump together near adsorbents, and the impact of folding when forming pleats caused the adhesive points to be cracked, and adsorbents dropped out from the filter medium for deodorizing filter. However, the use of the thermal bonded nonwoven made it denser between fibers than conventional adhesives and enabled adsorbents to be entangled and be adhered firmly. Thereby, the impact of folding made it difficult for the adhesive points to be cracked, and it became possible to prevent absorbents from dropping out.

Further, the present invention also includes the filter medium for deodorizing filter comprising the filter reinforcing material. More specifically, the filter medium for deodorizing filter of the present invention is characterized by comprising, the filter reinforcing material, the adsorbent layer comprising adsorbents laminated on the side of the bonding layer of the filter reinforcing material, and a base material laminated to sandwich the absorbent layer with the filter reinforcing material. The filter medium for deodorizing filter is, for example, pleated and preferably used as pleated air filters for automobiles, air conditioners, air purifiers and the like. In the filter medium for deodorizing filter, adsorbents may be sunk between the fibers forming the filter reinforcing material to some extent. Further, the base material and the bonding layer of the filter reinforcing material may be partially adhered. Further, the filter medium for deodorizing filter may have a design layer, a second adsorbent layer, a second filter reinforcing material and the like appropriately.

Hereinafter, the present invention will be described in detail.

<Filter Reinforcing Material>
<<Bonding Layer>>

The filter reinforcing material of the present invention comprises the bonding layer comprising the thermal bonded nonwoven including thermal bondable short fibers. The bonding layer has an adhesive function when joining the adsorbent layer comprising adsorbents and the filter reinforcing material. The bonding layer may comprise the same kind of thermal bondable short fibers or may comprise two or more different kinds of thermal bondable short fibers.

Fiber length of the thermal bondable short fibers is preferably 30 to 100 mm, more preferably 40 to 80 mm, and further preferably 45 to 70 mm.

More specifically, in the present description, the thermal bondable short fibers may be the fibers having a melting point 80 to 200° C., more preferably 95 to 190° C., and further preferably 100 to 180° C. Melting point of the thermal bondable short fibers is appropriately determined with a balance of heat resistance property and adhesive property of the reinforcing layer, absorbent and the base material as described later. Generally, the lower the melting point, the more the peel strength of the bonding layer, the integrally-processing property when manufacturing the filter medium for deodorizing filter, and the stiffness of the filter medium for deodorizing filter improve; the higher the melting point, the more the heat resistance property and the shape-keeping property of the filter medium for deodorizing filter improve.

It is preferable that the bonding layer comprises thermal bondable short fibers having a melting point of 80 to 150° C. by preferably 60 to 100 weight %, more preferably more than or equal to 75 weight %, further preferably more than or equal to 90 weight %, and more further preferably more than or equal to 95 weight % out of 100 weight % of fibers contained in the bonding layer. This condition will improve peel strength at the bonding layer, integrally-processing property at the time of making the filter medium for deodorizing filter, and stiffness of the filter medium for deodorizing filter.

To improve adhesive strength, the bonding layer comprises preferably more than or equal to 15 g/m$^2$, more preferably more than or equal to 20 g/m$^2$, preferably less than or equal to 60 g/m$^2$, more preferably less than or equal to 50 g/m², and further preferably less than or equal to 40 g/m² of thermal bondable short fibers having a melting point of 80 to 150° C.

On the other hand, even if the thermal bondable short fibers having a melting point of 80 to 150° C. are melted by heat treatment, the thermal bondable short fibers having a melting point of higher than 150° C. and lower than or equal to 200° C. are easy to retain their shapes because they are melted less than the thermal bondable short fibers having a melting point of 80 to 150° C. Thereby, that contributes to improving stiffness of the filter reinforcing material and the filter medium for deodorizing filter, retaining the shape of the bonding layer, and preventing apertures from expanding. For this reason, the bonding layer may comprise thermal bondable short fibers having a melting point of higher than 150° C. and lower than or equal to 200° C. In case of comprising thermal bondable short fibers having a melting point of higher than 150° C. and lower than or equal to 200° C., content of thermal bondable short fibers having a melting point of higher than 150° C. and lower than or equal to 200° C. is preferably 10 to 40 weight % out of 100 weight % of fibers contained in the bonding layer. However, if content of thermal bondable short fibers having a melting point of higher than 150° C. and lower than or equal to 200° C. increases too much, it may lead to a decrease in adhesive strength, therefore, the content is preferably less than or equal to 30 weight %, more preferably less than or equal to 20 weight %, and may be less than or equal to 1 weight %.

Fineness of thermal bondable short fibers may be appropriately selected according to the amount of treated air in the use environment of the filter medium for deodorizing filter and required dust collection performance, is preferably 1.0 to 40 dtex, and more preferably 1.5 to 30 dtex. For reference, the fineness of the thermal bondable short fibers refers to the fineness before heat treatment. For example, the fineness of the thermal bondable short fibers after heat treatment is usually 0.3 to 1 times of the fineness before heat treatment.

It is preferable that the bonding layer comprises two or more kinds of thermal bondable short fibers with a fineness difference of preferably more than or equal to 5 dtex, more preferably more than or equal to 8 dtex, further preferably more than or equal to 10 dtex, and preferably less than or equal to 30 dtex. Since fine thermal bondable short fibers contribute to increasing the number of bonded points in the bonding layer, the presence of the fine thermal bondable short fibers improves the adhesive strength. On the other hand, thick thermal bondable short fibers contribute to forming voids between fibers in the bonding layer and increasing strength of the filter reinforcing material, thus air permeability of the filter reinforcing material and bending rigidity of the filter medium for deodorizing filter may be improved.

For the same reason as above, fineness of the finer thermal bondable short fibers of the two types of thermal bondable short fibers with a fineness difference of more than or equal to 5 dtex (more preferably more than or equal to 8 dtex, and further preferably more than or equal to 10 dtex; hereinafter, sometimes referred to as "finer-fineness thermal bondable short fibers") is preferably 1.0 to 10 dtex, more preferably 1.5 to 7.0 dtex, and further preferably 1.8 to 5.0 dtex. On the other hand, fineness of the thicker thermal bondable short fibers (hereinafter, sometimes referred to as "thicker-fineness thermal bondable short fibers") is preferably more than 10 dtex and less than or equal to 40 dtex, more preferably 12 to 30 dtex, and further preferably 15 to 25 dtex.

Further, content ratio of the finer-fineness thermal bondable short fibers and the thicker-fineness thermal bondable short fibers is preferably 1:99 to 99:1, more preferably 15:85 to 60:40, and further preferably 20:80 to 45:55 as weight ratio (finer fineness thermal bondable short fibers:thicker-fineness thermal bondable short fibers). By adjusting the above range, the filter reinforcing material with a balance of adhesive strength and stiffness may be provided.

The examples used as thermal bondable short fibers are composite fibers, where a plurality of resins having different melting points are combined, with core-sheath structure, eccentric structure, or side-by-side structure; modified polyester fibers; modified polyamide fibers; modified polyolefin fibers such as modified polypropylene fibers and the like. The examples of the combination of resins used for the composite fibers are combination of polyolefin type such as polyethylene-polypropylene, polypropylene-modified polypropylene and the like, polyethylene-polyester, polyester-modified polyester, nylon-modified nylon or the like. Further, depending on the melting point, the thermal bondable short fibers consisting of a single resin may also be used.

Among them, the thermal bondable short fibers are preferably composite fibers with core-sheath structure, eccentric structure, or side-by-side structure. These composite fibers are made by combining a plurality of resins having different melting point. Therefore, after the thermal bondable short fibers are melted by heat, the low melting point component of the thermal bondable short fibers bonds and solidifies the fibers contained in the bonding layer, maintaining the high melting point component in the shapes of fibers. The high melting point component maintaining in the form of fibers contributes to high stiffness of the filter reinforcing material and improving filtration performance in the bonding layer.

The high melting point component of the composite fibers is exemplified by polyester resin such as polyethylene terephthalate, polybutylene terephthalate and the like; polyamide resin such as nylon 6, nylon 66 and the like. Among them, because of the wide variety of melting point and fineness and excellence of stiffness (high Tg) and heat resistance, polyester resin is preferable, and polyethylene terephthalate is particularly preferable.

The low melting point component of the composite fibers is preferably modified polyester or copolyester. The copolymerized component of the polyethylene terephthalate is exemplified by, for example, isophthalic acid, adipic acid, diethylene glycol, hexanediol and the like. Melting point of the low melting point component is preferably higher than or equal to 80° C., more preferably higher than or equal to 85° C., further preferably higher than or equal to 90° C., preferably lower than or equal to 170° C., more preferably lower than or equal to 160° C., and further preferably lower than or equal to 150° C.

Usually, weight ratio of the low melting point component and the high melting point component is preferably 30:70 to 70:30, more preferably 40:60 to 60:40, and further preferably 45:55 to 55:45.

For reference, as described later, since heat treatment is performed in the present invention, a part or a whole of the thermal bondable short fibers are present in a melted and solidified state in the bonding layer. The thermal bondable short fibers after being melted by heat, for example, may be solidified with the intertwisted points of the fibers contained in the bonding layer fixed. Further, the thermal bondable short fibers may exist in a state in which the entire thermal bondable short fibers are melted and solidified, and in case of using the composite fibers, they may exist in a state in which the high melting point component retain the shapes of fibers and the fibers contained in the bonding layer are bonded at the intertwisted points by the low melting point component.

The bonding layer may further comprise any fibers except for the thermal bondable short fibers as described above. The preferred optional fibers comprised in the bonding layer (except for the thermal bondable short fibers as described above) are non-bondable fibers. The non-bondable fibers are exemplified by, for example, natural fibers such as cotton, linen, wool, silk and the like; regenerated fibers such as rayon, polynosic, cupro, lyocell and the like; semisynthetic fibers such as acetate fibers, triacetate fibers and the like; polyamide fibers such as nylon 6, nylon 66, aramid fibers (para-aramid fibers, meta-aramid fibers and the like) and the like; polyester fibers such as polyethylene terephthalate fibers, polybutylene terephthalate fibers, polylactic acid fibers, polyarylate fibers and the like; acrylic fibers such as polyacrylonitrile fibers, polyacrylonitrile-vinyl chloride copolymer fibers and the like; polyolefin fibers such as polyethylene fibers, polypropylene fibers and the like; polyvinyl alcohol type fibers such as vinylon fibers, polyvinyl alcohol fibers and the like; polyvinyl chloride type fibers such as polyvinyl chloride fibers, vinylidene fibers, polychlal fibers and the like; synthetic fibers such as polyurethane fibers and the like; polyether type fibers such as polyethylene oxide fibers, polypropylene oxide fibers and the like. The bonding layer may comprise the same kind of the non-bondable fibers or two or more different kinds of the non-bondable fibers.

Cross-sectional shape of the non-bondable fibers is not particularly limited, and any of a circular cross section; a modified cross section such as triangle, a star, a pentagon and the like; can be used. Further, the non-bondable fibers may be either solid fibers or hollow fibers. Furthermore, the non-bondable fibers may be crimped fibers or non-crimped fibers.

The non-bondable fibers may be preferably short fibers, and fiber length of the fibers is preferably 10 to 300 mm, more preferably 20 to 100 mm. By adjusting the fiber length of the non-bondable fibers within the above range, the fibers cab be easily intertwisted.

Melting point of the non-bondable fibers is not particularly limited, but preferably higher than 200° C., more preferably higher than or equal to 220° C., further preferably higher than or equal to 240° C., more further preferably higher than or equal to 250° C., preferably lower than or equal to 400° C., more preferably lower than or equal to 350° C., and further preferably lower than or equal to 330° C. For reference, as for the non-bondable fibers that do not show clear melting point, melting point is defined by the decomposition temperature.

Fineness of the non-bondable fibers is not particularly limited, but 1.0 to 40 dtex, and more preferably 1.5 to 30 dtex.

Metsuke (mass per unit area) of the bonding layer is preferably 10 to 100 g/m$^2$, and more preferably 15 to 70 g/m$^2$.

<<Reinforcing Layer>>

The filter reinforcing material of the present invention comprises the reinforcing layer which comprises the nonwoven including high-melting fibers having a higher melting point than a melting point of the thermal bondable short fibers having the lowest melting point in the bonding layer by 30° C. or more. The reinforcing layer is installed in the most inlet layer or the most outlet layer of the filter medium for deodorizing filter.

For reference, the most inlet layer of the filter medium for deodorizing filter means the layer that, when a fluid flows, the fluid contacts first in the filter medium for deodorizing filter. Further, the most outlet layer of the filter medium for deodorizing filter means the layer that, when the fluid flows, the fluid contacts last in the filter medium for deodorizing filter.

The high-melting fibers mean the fibers that has a higher melting point than a melting point of the thermal bondable short fibers having the lowest melting point in the bonding layer by 30° C. or more. For example, if the melting point of the thermal bondable short fibers having the lowest melting point in the bonding layer is 110° C., the high-melting fibers in the reinforcing layer mean the fibers having a melting point of higher than or equal to 140° C.

The high-melting fibers are not particularly limited as long as they have the thermal bondable short fibers having the lowest melting point in the bonding layer, and are preferably exemplified by the thermal bondable short fibers having a higher melting point than a melting point of the thermal bondable short fibers having the lowest melting point in the bonding layer by 30° C. or more; the non-bondable fibers having a higher melting point than a melting point of the thermal bondable short fibers having the lowest melting point in the bonding layer by 30° C. or more. The thermal bondable short fibers and the non-bondable fibers that are preferably used for the reinforcing layer are exemplified by each of the thermal bondable short fibers and the non-bondable fibers as discussed in the section of the bonding layer.

The preferable high-melting fibers are the thermal bondable short fibers having a higher melting point than a melting point of the thermal bondable short fibers having the lowest melting point in the bonding layer by 30° C. or more, and having a melting point of higher than or equal to 150° C. and lower than or equal to 200° C.; or the non-bondable fibers having a melting point of higher than 200° C. and lower than or equal to 400° C. The thermal bondable short fibers are preferably composite fibers with core-sheath structure, eccentric structure, or side-by-side structure. Further, the non-bondable fibers are preferably polyester fibers.

It is preferable that the reinforcing layer comprises the high-melting fibers by preferably 60 to 100 weight %, more preferably more than or equal to 75 weight %, further preferably more than or equal to 90 weight %, and more further preferably more than or equal to 95 weight % out of 100 weight % of fibers contained in the reinforcing layer. The more the content of the high-melting fibers, the more it contributes to high stiffness of the filter reinforcing material, improvement of the integrally-processing property when manufacturing the filter medium for deodorizing filter and suppression of pleat adhesion at the time of pleating.

The nonwoven comprised in the reinforcing layer is not particularly limited as long as the nonwoven includes the high-melting fibers, but drylaid nonwoven such as a thermal bonded nonwoven, a resin-bonded nonwoven, a needlepunched nonwoven and the like; a spunlaid nonwoven; a meltblown nonwoven; a wetlaid nonwoven; and the like are preferably and appropriately used depending on the application. Among them, a thermal bonded nonwoven is preferable because of improving adhesive strength with the bonding layer.

The reinforcing layer may further comprise any fibers except for the high-melting fibers. The preferred optional fibers comprised in the reinforcing layer (except for the high-melting fibers) are exemplified by, for example, the low-melting fibers whose melting point satisfies higher than or equal to $T_L-10$(° C.) and lower than $T_L+30$(° C.) when melting point of the thermal bondable short fibers having the lowest melting point in the bonding layer is defined as $T_L$. To comprise the low-melting fibers is preferable since adhesive strength of the bonding layer and the reinforcing layer are improved. The low-melting fibers are exemplified by each of the thermal bondable short fibers as discussed in the section of the bonding layer. Among them, because of being excellent in adhesive property and stiffness, the low-melting fibers are preferably composite fibers with core-sheath structure, eccentric structure, or side-by-side structure. Further, for improving adhesive strength with the bonding layer, fineness of the low-melting fibers is preferably 1.0 to 40 dtex, and more preferably 10 to 25 dtex.

Metsuke of the reinforcing layer is preferably 10 to 100 g/m$^2$, and more preferably 15 to 70 g/m$^2$.

<<Property as the Filter Reinforcing Material>>

As discussed above, since the thermal bonded nonwoven is used as the bonding layer in the present invention, filtration performance is also exhibited in the bonding layer. Further, since the reinforcing layer corresponds to the most inlet layer or the most outlet layer (preferably the most inlet layer) in the filter medium for deodorizing filter, it is preferable that average fineness is changed between the bonding layer the reinforcing layer and density gradient of fibers are present between the bonding layer and the reinforcing layer. For example, the preferred embodiment is that average fineness of fibers contained in the reinforcing layer is larger than average fineness of fibers contained in the bonding layer. In the filter medium for deodorizing filter, the adsorbent layer is provided on the side of the bonding layer, thus the side of the reinforcing layer is often corresponding to the most inlet layer. In that case, dust with a large particle diameter is caught from the reinforcing layer to the bonding layer in order, thus it is possible to suppress to be directly adhered to adsorbents.

For reference, in the present invention, the average fineness of fibers contained in each layer is determined by weight average of all fibers contained in each layer.

Further, ratio of metsuke of the bonding layer and reinforcing layer (bonding layer:reinforcing layer) may be set arbitrarily within the range of 10:90 to 90:10. If the ratio of metsuke of the bonding layer is too high, the thermal fusion bondable component of the thermal bondable short fibers is melted by heat treatment and seep on the side of the reinforcing layer, thereby pleat adhesion may be caused at the time of heat setting. In that case, for preventing the thermal fusion bondable component bonding from seeping, it is preferable to adjust the average fineness, the density and the like of the reinforcing layer. On the other hand, if the ratio of metsuke of the reinforcing layer is too high, metsuke of the bonding layer cannot be secured sufficiently and adhesive strength with the adsorbent layer may decrease. For that, it is preferable that the thermal bondable short fibers are also mixed into the reinforcing layer.

Metsuke of the filter reinforcing material is preferably 20 to 200 g/m$^2$, more preferably 30 to 150 g/m$^2$, and further preferably 40 to 120 g/m$^2$.

Further, thickness of the filter reinforcing material is preferably 0.1 to 3.5 mm, more preferably 0.2 to 3.0 mm, and further preferably 0.3 to 2.5 mm.

If the metsuke and the thickness of the filter reinforcing material is within the range, moderate stiffness is provided and decrease in air flow rate of filter reinforcing material may be suppressed, and thereby pressure loss in the filter medium for deodorizing filter can be lowered. In particular, the thinner the filter reinforcing material, the better it is. This is because the number of the mountains of pleats can be increased and further, structural pressure loss by pleat contact can be suppressed.

Since the filter reinforcing material of the present invention has high stiffness and is excellent in pleating, it is also preferably used as the base material in the filter medium. If the filter reinforcing material of the present invention is used as the base material, the adhesives for fixing adsorbents is not required, thus the characteristic of the adsorbents can be utilized more effectively.

<<Process for Producing the Filter Reinforcing Material>>

Process for producing the filter reinforcing material comprises a laminating step of a fiber web for the bonding layer and a fiber web for the reinforcing layer, and a thermal bonding step of subjecting the laminated fiber webs to heat treatment.

When laminating the fiber webs used for the bonding layer and the reinforcing layer, after mixing the fibers contained in each layer, the general process for producing nonwoven, such as a parallel laying of the fiber web, that is spun from a carding machine, in a single layer or multiple layers as it is, or cross-laying of fiber web and the like, may be used.

It is desirable that heat treatment temperature in the thermal bonding step is preferably higher than the melting point of the all thermal bondable short fibers contained in the bonding layer and the reinforcing layer. After the thermal bonding step, a calendaring may be performed for adjusting the thickness of the filter reinforcing material. Because of this thermal bonding step, the bonding layer and the reinforcing layer are integrated by thermal fusion bonding.

Further, when producing the filter reinforcing material, it does not matter whether there is a mechanical bonding step such as needlepunching, hydroentangling and the like. In case where performing the mechanical bonding step after laminating the bonding layer and the reinforcing layer, it requires attention that the thermal bondable short fibers in the bonding layer do not penetrate to the surface on the reinforcing layer.

For adding functions to the filter reinforcing material, the produced filter reinforcing material may be resin processed using a liquid where various functional agents such as deodorant, air refresher, antibacterial agent, flame retardant, antiviral agent, fragrance, pigment and the like are dispersed in binder resin. As the binder resin, the general resins used for producing nonwoven may be used. The binder resin process may be performed by coating, impregnating and the like. For suppress deterioration of adhesive strength with the adsorbents, it is desirable that the binder resin comprising the functional agents are coated on the side of the reinforcing layer.

<Filter Medium for Deodorizing Filter>

<<Base Material>>

Base material used for the filter medium for deodorizing filter are preferably woven or nonwoven having air permeability, and particularly nonwoven is preferable because of being dense between fibers. Drylaid nonwoven such as a thermal bonded nonwoven, a needlepunched nonwoven, a spunlace nonwoven and the like; a spunlaid nonwoven; a meltblown nonwoven; a wetlaid nonwoven; and the like are preferably and appropriately used depending on the application as the nonwoven. The base material may be resin processed. Further, the base material may be electret processed.

The base material used for the filter medium for deodorizing filter is preferably the spunlaid nonwoven that is electret processed in terms of strength. The fibers contained in the spunlaid nonwoven are not particularly limited, and exemplified by polyolefin fibers such as polyethylene fibers, polypropylene fibers and the like; polyester fibers such as polyethylene terephthalate fibers, polybutylene terephthalate fibers, polylactic acid fibers, polyarylate fibers and the like; and the like.

Further, the base material used for the filter medium for deodorizing filter is also preferably the thermal bonded nonwoven that is resin processed. Considering heat shrinkage, the fibers, which do not have low melting point component, are usually mixed in the thermal bonded nonwoven at a fixed ratio. For that, the bonding at cross points is partly weak, and bending strength and tensile strength of the nonwoven as a whole are often insufficient. Therefore, by applying resin processing to the thermal bonded nonwoven, the entire cross points between the fibers are bonded, and it is possible to increase both bending strength and tensile strength.

The resins used for the resin processing are not particularly limited, the resins that are hard after processing are preferable, and acrylic resins such as acrylic acid ester-based resin, styrene-acrylic acid copolymer resin and the like; polyester resin; urethane resin; and the like may be used. Among them, in terms of hardness and heat resistance property, acrylic resins or polyester resin are preferable. The amount of resins used for resin processing is preferable 1 to 10 g/m$^2$, and more preferably 2 to 5 g/m$^2$. It is not preferable since sufficient stiffness cannot be exhibited if the amount of resins is small, and air permeability will be hindered if it is large. Further, at the time of resin processing, additional functional agents such as flame retardant, antibacterial antifungal agent, pigment and the like may be appropriately used. In particular, for improving visibility when dust is loaded and making it easy to know when to replace, mixing pigment is preferable.

<<Adsorbent Layer>>

The adsorbents contained in the adsorbent layer are exemplified by various adsorbents such as in powder form, in granular form, in crushed form, in granulated form, and in beaded form, and preferably activated carbon; silica gel; zeolite; and the like because of absorbing a wide variety of gases. It is suitable to use the activated carbon such as palm trees type, wood type, coal type, pitch type and the like. The number of the pores introduced into the inside that can be seen by observing the surface, so-called macropores, is preferably large. This is because, even if the thermoplastic powder resins cover the surface of the activated carbon when producing the mixed particulates from the activated carbon and the adhesives as described later (for example, thermoplastic powder resin), the absorbable pores can be open by desorbing the gas from the inner pores during hot pressing. Further, if the surface of the activated carbon is rough to a certain extent, the deterioration of the absorption performance may be suppressed since the fluidity of the melted resin is poor.

Considering the air permeability, the dropout of the adsorbents, sheet processing property and the like, the range of the particle diameter adsorbents is preferably 10 to 1000 μm, and more preferably 100 to 900 μm based on JIS Standard sieve (JIS Z8801). If the range of the particle diameter is less than 10 μm, pressure loss becomes too large for obtaining a certain high adsorption capacity, and further, since the packing density in the filter medium become high, rise of pressure loss when dust is loaded is fast to deteriorate the retaining amount of dust. If the range of the particle diameter is more than 1000 μm, it becomes easy to drop out from the filter medium, and further, the initial adsorbing performance by one-pass becomes extremely low. Furthermore, when being used as the filter unit for the air purification in the shape of pleats, waves and the like, bending and processing property during wavy processing may deteriorate. For reference, the above absorbents in granular powder form may obtained by adjusting the particle size to a specified level using an ordinary classifier.

The weight of the adsorbents in the filter medium for deodorizing filter is preferably 10 to 450 g/m$^2$, and more preferably 50 to 350 g/m$^2$. If it is within the above range, sufficient deodorizing performance may be exhibited while suppressing a large increase in pressure loss.

For the purpose of improving adsorbing performance of polar substance and aldehydes, the adsorbents may be used after chemical treatment. The preferable chemicals used for the gas chemical treatment toward the acid polar substances such as aldehyde type gas, nitrogen compounds such as NOx and the like, sulfur compounds such as SOx and the like, acetic acid and the like, are for example, amine type chemicals such as ethanolamine, polyethylenimine, aniline, p-anisidine, sulfanilic acid and the like, sodium hydroxide, potassium hydroxide, guanidine carbonate, guanidine phosphate, aminoguanidine sulfate, 5,5-dimethylhydantoin, benzoguanamine, 2,2-iminodiethanol, 2,2,2-nitrotriethanol, triethanolamine hydrochloride, 2-aminoethanol, 2,2-iminodiethanol hydrochloride, p-aminobenzoic acid, sodium sulfanilate, 1-arginine, methylamine hydrochloride, semicarbazide hydrochloride, hydrazine, hydroquinone, hydroxylamine sulfate, permanganate, potassium carbonate, potassium bicarbonate and the like; and toward the basic polar substances such as ammonia, methylamine, trimethylamine, pyridine and the like, are for example, phosphoric acid, citric acid, malic acid, ascorbic acid, tartaric acid and the like. For reference, the chemical treatment is performed by, for example, carrying or adding the chemicals on the adsorbents. Further, besides the method of treating the adsorbents with the chemicals directly, there may be a method of adding near the surface of the filter medium by the general coating method and the like or a method of adding on the entire filter medium by impregnation. At that time, there may be a method of preparing the chemical aqueous solution mixed with the thickener such as sodium alginate, polyethylene oxide and the like, to carry or add this. This method is also effective for carrying or adding the chemicals having a low solubility in water, further for suppressing the drop of the chemicals.

The adsorbent layer further comprises adhesives. The adhesives are, for example, thermoplastic powder resin, hot-melt sheet (for example, hot-melt sheet with a cobweb shape; "Dynac (registered trademark)" manufactured by Kureha Ltd.) and the like, among them, thermoplastic powder resin is preferable. The powder resin may be uniformly dispersed to the adsorbents. The thermoplastic powder resin is exemplified by polyolefin-based resin, polyamide-based resin, polyester-based resin, ethylene-acrylic acid copolymer resin, ethylene-vinyl acetate copolymer resin and the like.

The size of the thermoplastic powder resin used as the adhesives is preferably 10 to 500 μm, and more preferably 20 to 400 μm in average particle diameter. It is desirable to be comprised higher than or equal to 95 weight % in the range of the average particle diameter of 10 to 500 μm. If the average particle diameter is within the above range, it is possible to prevent the thermoplastic resin from blocking the surface pores of the adsorbents in granular powder form. Additionally, when mixing with the adsorbents, pre-bonding with the adsorbents in granular powder form by van der Waals force or electrostatic force may be performed effectively, it may be dispersed uniformly, and thereby it is possible to prevent partial peeling of the adsorbent layer and the base material effectively.

The shape of the thermoplastic powder resin used for the adhesives is not particularly determined, and exemplified by spherical type, crushed type and the like. Needless to say, two or more kinds of the thermoplastic powder resin may be used together. Furthermore, in case of using the adsorbents in granular powder form carrying chemicals or the base material carrying chemicals, with this method, since the surface of the adsorbents in granular powder form becomes in a state in which the thermoplastic powder resin is temporarily bonded from the time of mixing in a dry state, even if the chemicals have different properties, they may be prevented from interfering with each other in the subsequent process for forming sheet, so that sufficient effect may be exhibited.

The thermoplastic powder resin is used preferably in amount of 1 to 40 weight %, and more preferably in amount of 3 to 30 weight % with respect to the adsorbents. If it is within the above range, it is possible to produce the filter medium for deodorizing filter that is excellent in adhesive strength with the base material, pressure loss, and deodorizing performance.

<<Property as the Filter Medium for Deodorizing Filter>>

The filter medium for deodorizing filter may be constituted by comprising the components having ancillary functions such as antibacterial agent, antifungal agent, antiviral agent, flame retardant and the like. These components may be kneaded into the fibers or nonwoven, or may be added and carried by the post processing. For example, by being constituted by comprising the flame retardant, it is possible to produce the filter medium for deodorizing filter that conforms to the flame retardant standard defined in fMVSS.302 and UL flame retardant standard.

The method how the filter medium for deodorizing filter is hot pressed to finally make a sheet is exemplified by the methods used generally in this field such as a method of hot pressing between rollers, or a method of flatbed laminating to be sandwiched between the heated belt conveyors which are flat both upper and lower, and the like. The flatbed laminating method is preferable to create a more uniform thickness and an adhesive state.

The process for producing the filter medium for deodorizing filter will be discussed in detail. First, weighing the adsorbents and the adhesives with a predetermined weight, putting them in a stirrer, and stirring for about 10 minutes with a rotating speed of 30 rpm are performed. Next, the mixed powder is sprayed on the side of the bonding layer of the filter reinforcing material, further the base material is overlaid from above, and hot pressing process is performed; or, the mixed powder is sprayed on the base material, overlaying is further performed from above so that the side of the base material sprayed with the mixed powder faces the side of the bonding layer of the filter reinforcing material, and hot pressing process is performed. It is preferable that the surface temperature during hot pressing is 3 to 30° C., and preferably 5 to 20° C. higher than the melting point of the thermoplastic resin.

Thickness of the filter medium for deodorizing filter is preferably 0.1 to 3.0 mm, and more preferably 0.5 to 2.0 mm. If thickness is less than 0.1 mm, because of the small dust collection space, rise of pressure loss when dust is loaded is fast to cause clogging. On the other hand, if thickness is more than 3.0 mm, structural resistance becomes large when it is used as a pleated unit since the entire filter medium is too thick. As a result, that leads to a practical problem that pressure loss of the entire unit becomes too high.

Metsuke of the filter medium for deodorizing filter is preferably 30 to 500 g/m$^2$. If metsuke is less than 30 g/m$^2$, because of the small stiffness of the filter medium, pressure loss increases due to the deformation of the unit when ventilation is loaded. If metsuke is more than 500 g/m$^2$, the filter medium becomes thick, thus there is a practical problem that structural resistance becomes large when it is used as a pleated unit Thickness of the pleated filter unit using the filter medium for deodorizing filter is preferably 5 to 400 mm. Considering the storage space, about 10 to 60 mm is preferable for in-vehicle use such as built-in and installed-in the car air conditioner and household air purifiers, and about 40 to 400 mm is preferable for a large filter unit installed for the building air conditioning.

When the filter medium for deodorizing filter is subjected to pleating, general pleating machines such as a reciprocate type or a rotary type and the like may be used. Further, for making it easier to attach the frame material with fixing the height and pitch of the pleats, additionally for the shape stability of the filter medium for deodorizing filter in use, heat setting step may be performed. Heat treatment temperature at the time of heat setting may be preferably set to higher than or equal to the melting starting temperature (about melting point −10 to 20° C.) of the thermal bondable short fibers contained in the bonding layer and lower than or equal to the melting point of the thermal bondable short fibers contained in the bonding layer +30(° C.). Thereby, the shapes of pleats may be maintained without pleat adhesion of pleats, and performance of the filter medium for deodorizing filter itself may also be maintained.

The present application claims for benefit of priority based on JP Patent Application No. 2018-0043778 filed on Mar. 12, 2018. The entirety of the specification of JP Patent Application No. 2018-043778 filed on Mar. 12, 2018 is incorporated herein for reference.

EXAMPLES

Hereinafter, the present invention will be described more specifically by way of examples. The present invention is not limited to examples described below, and can also be carried out with appropriate modifications within the range adaptable to the gist described above and below, and such modifications are included in the technical scope of the present invention. For reference, in the following, unless otherwise noted, "part" means "weight part", and "%" means "weight %".

Evaluations of Examples and Comparative examples are as follows.

1. Metsuke (mass per unit area): According to JIS L1913 6.2.
2. Thickness: According to JIS L1913 6.1.1 A method. The pressure applied to test piece is 2 g/cm$^2$.
3. Peel strength: The filter medium for deodorizing filter is used and measured according to JIS L1086 7.10. The size of the test piece is 50 mm wide, and 200 mm long. Peeling speed is 100 mm/min.
4. Bending strength: As a sample, the filter medium for deodorizing filter cut to a size of 80 mm in length×65 mm in width is used. When preparing the sample, length and width of the sample are made corresponding to the machine direction (MD) and cross machine direction (CD) of the fiber sheet, respectively. The sample is folded with a mountain fold at the half position from both ends in length direction, so that the sample is made a size of 40 mm in length×65 mm in width. In a state in which the mountain parts of the folded sample is turned upwards, it is set in a rectangular frame with a size of 40 mm in length×65 mm in width, so that length direction and width direction of the sample are corresponding to length direction and width direction of the frame, respectively. On the other hand, the compression jig with a tip of φ10 mm is attached to the upper grip of the tensile testing machine. The compression jig is pressed against the center of the mountain parts of the sample in the width direction and moved downward at a speed of 50 mm/min. The load at that time is measured, and the maximum measured value is determined as the bending strength.

5. Peeling at the time of pleating: The filter medium for deodorizing filter was slit to a width of 250 mm, and creased so that a height of pleats was 28 mm, and the pleats were formed. The peeling state at that time is evaluated using the following symbols.
A: No Peeling occurred, the mountain parts and the valley parts of the pleats were quite sharp, and the pleats were fairly neat.
B: Peeling did not occur, the mountain parts and the valley parts of the pleats were sharp, and the pleats were neat.
C: Some peeling occurred or there were some peeling-like parts, and there were some parts where the mountain parts and the valley parts of the pleats were not sharp or the pleats were not neat. (Standard)
D: A lot of peeling occurred and it could not be processed, and there were a lot of parts where the mountain parts and the valley parts of the pleats were not sharp or the pleats were not neat.

6. Pleat adhesion at the time of heat setting: After the evaluation of "5. Peeling at the time of pleating", heat setting is performed at the temperature shown in Table, and "Pleat adhesion at the time of heat setting" is evaluated using the following symbols.
B: Pleat adhesion did not occur. The shape of pleats and pleating property were good.
D: Pleat adhesion occurred. The shape of pleats and pleating property were bad.

7. Shape after heat setting: After the evaluation of "5. Peeling at the time of pleating", heat setting is performed at the temperature shown in Table, and "Shape after heat setting" is evaluated using the following symbols.
A: Pleats were regularly arranged in good order, and the shape of pleats and pleating property were quite good.
B: Pleats were almost regularly arranged in good order, and the shape of pleats and pleating property were good.
C: There were some parts where pleats were not regularly arranged, but the shape of pleats and pleating property were practical level. (Standard)
D: There were many parts where pleats were not regularly arranged, and the shape of pleats and pleating property were bad.

8. Pressure loss of the unit: After the evaluation of shape after heat setting, general-purpose frame materials are attached to four sides to produce a unit of pleated air filter. Pressure loss (Ps) in Examples and Comparative examples is evaluated using the following symbols by difference from pressure loss (Ps') in Reference example which corresponds to standard.
A: Decreasing rate of pressure loss was higher than 5%, and quite better than standard.
B: Decreasing rate of pressure loss was higher than 0% and lower than or equal to 5%, and more than or equal to standard.
C: Standard
D: Pressure loss was larger than standard.
For reference, decreasing rate of pressure loss (%)=(Ps'-Ps)/(Ps')×100.

9. Comprehensive evaluation: Whether it is suitable as a pleated air filter or not is evaluated using the following symbols.
A: Quite suitable as the pleated air filter
B: Suitable as the pleated air filter
C: A little problem as the pleated air filter (standard)
D: Not suitable as the pleated air filter Fibers used in Examples and Comparative examples of the present application are summarized below. For reference, the thermal bondable short fibers (a) to (e) are polyester fibers with core-sheath structure having a composition ratio of 50(core)/50(sheath), and are the fibers of which core component is polyethylene terephthalate and of which sheath component is modified polyester having a melting point shown in Table 1 below.

TABLE 1

| Fibers | Components | Structure | Melting point (° C.) | Fineness (dtex) | Fiber length (mm) |
|---|---|---|---|---|---|
| Thermal bondable fiber (a) | Polyester | Core-sheath | 110 | 2.2 | 51 |
| Thermal bondable fiber (b) | Polyester | Core-sheath | 110 | 17 | 51 |
| Thermal bondable fiber (c) | Polyester | Core-sheath | 150 | 4.4 | 51 |
| Thermal bondable fiber (d) | Polyester | Core-sheath | 150 | 2.2 | 51 |
| Thermal bondable fiber (e) | Polyester | Core-sheath | 180 | 22 | 64 |
| PET fiber (f) | Polyester | Single | 260 | 17 | 51 |

Example 1

As the bonding layer and the reinforcing layer, weighing and mixing were performed according to each the fibers and weight ratio shown in Table to produce cross-laid fiber webs, and then laminated. After laminating, heat treatment was performed for 30 seconds at a heat treatment temperature of 200° C. to produce the filter reinforcing material.

On the side of the bonding layer of the produced filter reinforcing material, 280 g/m² of the functional material, which is a mixture of the coconut shell activated carbon (average particle diameter 400 μm) and the polyester-based thermoplastic resin powder (particle size distribution 100 to 150 μm) with a weight ratio of 1:0.05, was sprayed. After spraying the EVA-based thermoplastic resin powder on that, the base material which is consisted of the electret processed spunlaid nonwoven made of polypropylene (PP) was laminated, and heat treatment at 130° C. shown in Table 2 for integrating, to produce the filter medium for deodorizing filter.

Examples 2 to 8 and Comparative Examples 1 to 2

In the same manner as Example 1 except that the conditions shown in Table 2 were changed, the filter reinforcing material and the filter medium for deodorizing filter were manufactured.

Reference Example

As the reinforcing layer, weighing and mixing were performed according to the fibers and weight ratio shown in Table 2 to produce cross-laid fiber webs, heat treatment was performed for 30 seconds at a heat treatment temperature of 200° C. On that, the polyester type thermal bondable filament nonwoven (Dynac™: melting point 120° C.) was laminated as the bonding layer, heat treatment was performed at 140° C. to produce the filter reinforcing material.

TABLE 2

| | | | | Ex. 1 | Ex. 2 | Ex. 3 | Ex. 4 | Ex. 5 | Ex. 6 | Ex. 7 | Ex. 8 | Co. 1 | Co. 2 | Ref. |
|---|---|---|---|---|---|---|---|---|---|---|---|---|---|---|
| Filter reinforcing material | Constitution | Bonding layer | Thermal bondable fibers (a) 110° C. 2.2dtex (%) | 30 | 70 | 30 | 30 | 30 | 30 | 30 | 30 | 30 | 0 | 0 |
| | | | Thermal bondable fibers (b) 110° C. 17dtex (%) | 70 | 30 | 50 | 50 | 70 | 70 | 70 | 70 | 70 | 0 | 0 |
| | | | Thermal bondable fibers (c) 150° C. 4.4dtex (%) | 0 | 0 | 0 | 0 | 0 | 0 | 0 | 0 | 0 | 35 | 0 |
| | | | Thermal bondable fibers (e) 180° C. 2.2dtex (%) | 0 | 0 | 20 | 20 | 0 | 0 | 0 | 0 | 0 | 65 | 10 |
| | | | Dynac™ (%) | — | — | — | — | — | — | — | — | — | — | 10 |
| | | | Metsuke of thermal bondable short fibers with a melting point of 80 to 150° C. (g/m²) | 36 | 25 | 29 | 29 | 37 | 40 | 18 | 60 | 35 | 0 | 0 |
| | | | Metsuke of bonding layer (g/m²) | 36 | 25 | 36 | 36 | 37 | 40 | 18 | 60 | 35 | 35 | 10 |
| | | Reinforcing layer | Thermal bondable fibers (a) 110° C. 2.2dtex (%) | 0 | 0 | 0 | 0 | 0 | 0 | 20 | 0 | 30 | 0 | 0 |
| | | | Thermal bondable fibers (b) 110° C. 17dtex (%) | 0 | 0 | 0 | 20 | 0 | 0 | 0 | 0 | 70 | 0 | 0 |
| | | | Thermal bondable fibers (c) 150° C. 4.4dtex (%) | 35 | 35 | 35 | 35 | 30 | 35 | 30 | 0 | 0 | 35 | 35 |
| | | | Thermal bondable fibers (d) 150° C. 2.2dtex (%) | 0 | 0 | 0 | 0 | 0 | 0 | 0 | 100 | 0 | 0 | 0 |
| | | | Thermal bondable fibers (e) 180° C. 2.2dtex (%) | 65 | 65 | 65 | 45 | 50 | 65 | 50 | 0 | 0 | 65 | 65 |
| | | | PET fibers (f) 260° C. 17dtex (%) | 0 | 0 | 0 | 0 | 20 | 0 | 0 | 0 | 0 | 0 | 0 |
| | | | Mixing ratio of high-melting fibers (%) | 100 | 100 | 100 | 80 | 100 | 100 | 80 | 100 | 0 | 0 | — |
| | | | Metsuke of reinforcing layer (g/m²) | 35 | 25 | 35 | 35 | 35 | 32 | 54 | 10 | 35 | 36 | 60 |
| | | Total | Total metsuke (bonding layer + reinforcing layer) (g/m²) | 71 | 50 | 71 | 71 | 72 | 72 | 72 | 70 | 70 | 71 | 70 |
| | | | Bonding layer: Reinforcing layer (ratio of metsuke) | 50:50 | 50:50 | 51:49 | 51:49 | 51:49 | 56:44 | 25:75 | 86:14 | 50:50 | 50:50 | 14:86 |
| | Manufacturing conditions | | Heat treatment temperature (° C.) | 200 | 200 | 200 | 200 | 200 | 200 | 200 | 200 | 200 | 200 | 200 |
| Filter medium for deodorizing filter | Constitution | | Metsuke of (adsorbents + adhesive resin) (g/m²) | 280 | 280 | 280 | 280 | 280 | 280 | 280 | 280 | 280 | 280 | 280 |
| | | | Metsuke of base material (g/m²) | 20 | 20 | 20 | 20 | 20 | 20 | 20 | 20 | 20 | 20 | 20 |
| | | | Materials for base material | PP | PP | PP | PP | PP | PP | PP | PP | PP | PP | PP |
| | Manufacturing conditions | | Heat treatment temperature | 130 | 130 | 130 | 130 | 130 | 130 | 130 | 130 | 130 | 130 | 130 |
| Pleated unit | Manufacturing conditions | | Temperature at the time of heat setting (° C.) | 100 | 100 | 100 | 100 | 100 | 100 | 100 | 100 | 100 | 100 | 100 |
| | Property | | Thickness (mm) | 1.0 | 0.8 | 1.0 | 1.0 | 1.1 | 1.0 | 1.0 | 1.1 | 1.0 | 1.3 | 1.0 |
| | | | Peel strength (N/50 mm) | 2.06 | 2.00 | 1.80 | 1.85 | 2.06 | 2.21 | 1.55 | 2.30 | 2.08 | 0.66 | 1.50 |
| | | | Bending strength (N) | 1.50 | 1.15 | 1.35 | 1.45 | 1.43 | 1.59 | 1.33 | 1.54 | 1.53 | 0.43 | 1.20 |
| | | | Peeling at the time of pleating | A | A | A | A | A | A | B | A | A | D | C |
| | | | Pleat adhesion at the time of heat setting | B | B | B | B | B | B | B | B | D | D | B |
| | | | Shape after heat setting | A | A | A | A | A | A | B | A | D | D | B |
| | | | Pressure loss of the unit | A | A | A | A | A | A | B | B | D | D | C |
| | | | Comprehensive evaluation | A | A | A | A | A | A | B | B | D | D | C |

The invention claimed is:

1. A filter reinforcing material comprising,
a bonding layer comprising a thermal bonded nonwoven including thermal bondable short fibers, and
a reinforcing layer comprising a nonwoven including high-melting fibers having a higher melting point than a melting point of thermal bondable short fibers having the lowest melting point in the bonding layer by 30° C. or more,
wherein Metsuke of the filter reinforcing material is 40 to 120 g/m$^2$, and
the high-melting fibers comprise at least one selected from the group of (a) thermal bondable short fibers having a fineness of 1.0 to 40 dtex and a higher melting point than a melting point of the thermal bondable short fibers having the lowest melting point in the bonding layer by 30° C. or more and (b) non-bondable fibers having a fineness of 1.0 to 40 dtex and a higher melting point than a melting point of the thermal bondable short fibers having the lowest melting point in the bonding layer by 30° C. or more.

2. The filter reinforcing material according to claim 1, wherein the bonding layer comprises two or more kinds of thermal bondable short fibers with a fineness difference of more than or equal to 5 dtex.

3. The filter reinforcing material according to claim 1, wherein the reinforcing layer comprises the high-melting fibers by more than or equal to 60 weight % out of 100 weight % of fibers contained in the reinforcing layer.

4. The filter reinforcing material according to claim 1, wherein,
melting point of the thermal bondable short fibers in the bonding layer is 80 to 150° C., and
content of the thermal bondable short fibers in the bonding layer with a melting point of 80 to 150° C. is 60 to 100 weight % out of 100 weight % of fibers contained in the bonding layer.

5. The filter reinforcing material according to claim 1, wherein average fineness of fibers contained in the reinforcing layer is larger than average fineness of fibers contained in the bonding layer.

6. The filter reinforcing material according to claim 1, wherein the bonding layer and the reinforcing layer are integrated by thermal fusion bonding.

7. The filter reinforcing material according to claim 1, wherein the thermal bondable short fibers in the bonding layer are composite fibers with core-sheath structure, eccentric structure, or side-by-side structure.

8. A filter medium for deodorizing filter comprising,
the filter reinforcing material according to claim 1,
an adsorbent layer comprising adsorbents laminated on the side of the bonding layer of the filter reinforcing material, and
a base material laminated to sandwich the adsorbent layer with the filter reinforcing material.

* * * * *